(12) United States Patent
Bouillon et al.

(10) Patent No.: US 7,556,036 B2
(45) Date of Patent: Jul. 7, 2009

(54) ANESTHESIA DEVICE, SYSTEM AND METHOD

(75) Inventors: Thoasm Bouillon, Bern (CH); Peter Schumacher, Kirchlindach (CH)

(73) Assignee: Dräger Medical AG & Co. KG, Lübeck (DE)

( * ) Notice: Subject to any disclaimer, the term of this patent is extended or adjusted under 35 U.S.C. 154(b) by 568 days.

(21) Appl. No.: 11/250,026

(22) Filed: Oct. 13, 2005

(65) Prior Publication Data

US 2006/0081244 A1    Apr. 20, 2006

(30) Foreign Application Priority Data

Oct. 19, 2004   (DE) ...................... 10 2004 050 717

(51) Int. Cl.
*A61M 16/01* (2006.01)
*A61M 16/00* (2006.01)

(52) U.S. Cl. .......................... 128/203.15; 128/203.12; 128/200.24

(58) Field of Classification Search ............ 128/203.12, 128/203.13, 203.14, 203.22, 204.21, 204.23, 128/204.12, 200.24; 600/310–314; 604/503, 604/504, 512
See application file for complete search history.

(56) References Cited

U.S. PATENT DOCUMENTS

| | | | | |
|---|---|---|---|---|
| 5,537,993 | A | * | 7/1996 | Reichert et al. ........ 128/203.14 |
| 5,925,014 | A | * | 7/1999 | Teeple, Jr. .................. 358/1.15 |
| 2003/0176804 | A1 | * | 9/2003 | Melker ...................... 600/532 |

OTHER PUBLICATIONS

St. Pierre et al. Awareness during laryngoscopy and intubation: quantitating incidence following induction of balanced anesthesia with etomidate and cisatracurium as detected with the isolated forearm technique, Journal of Clinical Anesthesia vol. 12, Issue 2, Mar. 2000, pp. 104-108).*

(Continued)

*Primary Examiner*—Justine R Yu
*Assistant Examiner*—Arundipta Shome
(74) *Attorney, Agent, or Firm*—McGlew and Tuttle, P.C.

(57) ABSTRACT

An anesthesia device has a device (4, 5) for the supply of at least one first anesthetic and a second anesthetic in a quantitatively settable, controlled manner. A data processing unit (6) with a corresponding display (8) is set up for determining the current concentrations in the plasma or at the site of action from continuously supplied data on the quantities of the anesthetics administered with a module (10) for a pharmacokinetic compartment model calculation and for storing these concentration values. Concentration data is predicted for at least one point in time in the future and this is also calculated. An action module (20) keeps ready the curve of at least one anesthesia action parameter as a function of the concentrations of the anesthetics in a stored manner. A display module (30) displays on the display (8) at least one action diagram, in which the concentration of the first or second anesthetic as well as the sequence of the concentration data of the anesthesia curve obtained up to that point in time are displayed and the predicted concentration data are displayed with a separate symbol. In case of comparison with concentration set points, it is also possible to act automatically on the feed of the anesthetics in a controlled manner with the predicted concentrations.

2 Claims, 4 Drawing Sheets

OTHER PUBLICATIONS

Liu et al. (EEG Bispectral analysis predicts the depth of Midzolam induced sedation, Anesthesiology, 84(1): 64-69, Jan. 1996.).*

Eger (Age, minimum alveolar anesthetic concentration, and minimum alveolar anesthetic concentration- awake, Anesthesiology Analg. 2001; 93:947-953).*

Mertens et al. (Predictive performance of computer-controlled infusion of remifentanil during propofol/remifentanil anaesthesia. Br J Anaesth. Feb. 2003;90(2):132-41.) teaches predictive performance of the available pharmacokinetic parameter sets for remifentanil, when used for target-controlled infusion (TCI) during total i.v. anaesthesia.*

Minto et al. (Response surface modelling of drug interactions, Adv Exp Med Biol. 2003;523:35-43.) also teaches additional methods of response surface modeling.*

Greco et al., Sep. 1, 1990, *Application of a New Approach for the Quantitation of Drug Cancer Research 50,* 5318-5327.

Minto et al., Jun. 2000, *Response Surface Model for Anesthetic Drug Interactions Anesthesiology 2000;* 92:1603-16.

Bouillon, M.D. et al., Jun. 2004, *Pharmacodynamic Interaction between Propofol and Anesthesiology 2004;* 100:1353-72.

Carpenter et al., 1986, *Pharmacokinetics of Inhaled Anesthetics Anesth Analg,* 1986; 65:575-82.

Yasuda, M.D. et al., 1991, *Comparision of Kinetics of Sevoflurane and Anesth Analg,* 1991; 72:316-24.

Yasuda, M.D. et al., 1991, *Kinetics of Desflurane, Isoflurane, and Anesthesiology 74*:489-498, 1991.

Syroid et al., Mar. 2002, *Development and evaluation of a graphical anesthesia drug display Anesthesiology,* vol. 96, No. 3.

* cited by examiner

ANESTHESIA DEVICE, SYSTEM AND METHOD

CROSS REFERENCE TO RELATED APPLICATIONS

This application claims the benefit of priority under 35 U.S.C. § 119 of German Application DE 10 2004 050 717.1 filed Oct. 19, 2005, the entire contents of which are incorporated herein by reference.

FIELD OF THE INVENTION

The present invention pertains to an anesthesia device, system and method with which at least two different anesthetics can be fed to a patient in settable quantities.

BACKGROUND OF THE INVENTION

The combined use of a plurality of different anesthetics is common practice in modern anesthesia technique. The task of the anesthesiologist is to set the dosages of the individual anesthetics and thus to control the course of the anesthesia. The action of the combined anesthetics does not correspond, as a rule, to the sum of the individual actions, but there are interactions. This makes the setting of the dosages of the individual anesthetics a complicated task.

Based on the concentrations of the active ingredients at the site of the action, it is now possible to estimate an action on the basis of common interaction models. The data on which the model is based are usually obtained experimentally in studies on patients and volunteers and analyzed by means of statistical methods to form a model (compare, e.g., Greco W. R. et al., Application of a new approach for the quantitation of drug synergism to the combination of cis-diaminoedichloroplatinum and 1-beta-D-arabinofuranosylcytosine, *Cancer Res.*, 1990, Sep. 1; 50(17):5318-27 Minto C. F. et al., Response surface model for anesthetic drug interactions. *Anesthesiology*, 2000, June 92(6), 1603-1616; Bouillon T. W. et al., Pharmacodynamic interaction between propofol and remifentanil regarding hypnosis, tolerance of laryngoscopy, bispectral index, and electroencephalographic approximate entrophy, *Anesthesiology*, June 2004; 100 (6): 1353-1372).

A certain value is obtained for each pair of concentration values from the interaction of two anesthetics for a certain anesthesia action parameter, e.g., for the probability that laryngoscopy will be tolerated. If the concentrations of two anesthetics are plotted on the X and Y axes, an action or response surface will then be obtained, as it is shown, e.g., in FIG. 2 for the probability of the tolerance of laryngoscopy (TOL), left-hand figure, and the tolerance to shaking and shouting (TOSS), right-hand figure. A horizontal section through the response surface yields a curve, on which the particular anesthesia action parameter has the same value. These lines of equal action are called isoboles.

The concentrations of the anesthetics at the site of action or in the plasma can be calculated from the quantities of the anesthetics fed by means of so-called pharmacokinetic compartment models. The concentrations for intravenous anesthetics are calculated, for example, with two- to three-compartment models. Such a pharmacokinetic compartment model is schematically shown in FIG. 1. These models always comprise a central compartment, which corresponds to the concentration in the plasma. An effect compartment is usually attached to the central compartment in order to model the transport to the site of action and the duration of action of the anesthetic, which is associated therewith. Five-compartment models, with which especially the concentration in the compartment rich in vessels—which includes the brain (site of action)—can be approximated, are used for gaseous anesthetics (compare, e.g., Carpenter R. I. et al., Pharmacokinetics of inhaled anesthetics in humans: measurements during and after the simultaneous administration of enflurane, halothane, isoflurane, methoxyflurane, and nitrous oxide, *Anesth. Analg.*, June 1986; 65 (6): 575-582; Yasuda N. et al., Comparison of kinetics of sevoflurane and isoflurane in humans. *Anesth. Analg.*, March 1991; 72 (3): 316-324; Yasuda N. et al., Kinetics of desflurane, isoflurane, and halothane in humans, *Anesthesiology*, March 1991; 74 (3): 489-498).

The most advanced attempt at facilitating the handling of anesthesia devices during the administration of a plurality of drugs is described in the article "Development and evaluation of a graphical anesthesia drug display," Noah D. Syroid et al., *Anesthesiology*, Vol. 96, No. 3, March 2002. It is proposed there that the concentration of the individual drugs be approximated, recorded and extrapolated into the future by means of pharmacokinetic compartment models. Furthermore, the individual concentration curves are always represented on a display means as a curve as a function of the time. In addition, bar graphs, in which the individual contributions of each drug are shown next to each other in the form of a differently colored bar, are provided for certain anesthesia action parameters. In addition, the contribution of synergistic interaction to the action parameter is plotted on a gray area.

SUMMARY OF THE INVENTION

The object of the present invention is to provide an anesthesia device, system and method wherein the device can be controlled by an anesthesiologist more easily and reliably during the feed of a plurality of anesthetics.

According to the invention, an anesthesia device, is provided with means for feeding at least a first and a second anesthetic in settable quantities. A data processing means is provided along with a corresponding display means. The data processing means is set up with a module for a pharmacokinetic compartment model calculation, which is set up to determine current concentrations in the plasma or at the site of action and to store them continuously as a time sequence of concentration data, wherein concentration data of the first and second anesthetics predicted for at least one point in time in the future are also calculated by means of the pharmacokinetic compartment model calculation module under the assumption of a feed continued in a defined manner. An action module is set up to keep ready the curve (response surface) for at least one anesthesia action parameter as a function of the concentrations of the first and second anesthetics in a stored manner. A display module is set up to display on the display means at least one action diagram, in which the concentrations of the first and second anesthetics are displayed on the x axis and the y axis, respectively, wherein a view of the response surface is superimposed to the x-y system of coordinates, as well as the sequence of the concentration data of the anesthesia up to that point in time is displayed as a trajectory and the predicted concentration data are displayed with a separate symbol.

The data of the quantities of at least one first anesthetic and at least one second anesthetic, which are fed per unit of time, are accordingly passed on to the data processing means. The data processing means is provided with a module for a pharmacokinetic compartment model calculation, which is set up to predict the current concentration in the plasma and at the site of action of the first and second anesthetics fed from the data entered for the quantities of the first and second anesthetics fed and to continuously store this concentration value as a time sequence of concentration data. Moreover, the pharmacokinetic compartment model calculation module is used for prognosis at least for one point in time in the future, based on the assumption of a feed of the first and second anesthetics which is continued in a defined manner. Furthermore, the data processing means is provided with an action module, which is set up to keep ready in a stored manner the course (response surface) at least for one anesthesia action parameter as a function of the concentration of the first and second anesthetics. Furthermore, a display module is provided, which is set up to display on the display means at least one action diagram, in which the concentrations of the respective first and second anesthetics are plotted on the x and y axes, wherein a representation of the response surface is superimposed to the x-y system of coordinates thus formed, and the sequence of the concentration data of the course of anesthesia that has taken place so far is displayed as a trajectory, and the predicted concentration data are displayed with a separate symbol.

In a preferred embodiment, the response surface for an anesthesia action parameter is superimposed to the x-y system of coordinates of the concentrations by projecting the response surface onto the plane of the x-y system of coordinates, which is performed by displaying a plurality of isoboles of the response surface, wherein the surfaces separated by one isobole are colored differently. It is thus possible, for example, to represent areas of the anesthesia action that are dangerous and are to be avoided for any reason by a highlighted or alarming color or in red, while noncritical areas can be increasingly represented in other colors, e.g., in yellow, light green and green. The anesthesia curve is then represented as a succession of pairs of concentration values in the plane of the x-y system of coordinates, the succession of the individual values forming a trajectory of the anesthesia curve. One or more points in the future with predicted concentration data can also be displayed with separate symbols beyond the end point of the trajectory, which represents the current point in time.

The anesthesia device can thus be handled by the anesthesiologist more simply and reliably, because the course of the anesthesia is simpler and directly intuitive concerning the current state of the patient with respect to the dispensing of the anesthetic. Furthermore, the course of the trajectory up to a current point in time as well as the representation of concentration values extrapolated into the future make possible the intuitive, direct estimation of the further course, which enables the anesthesiologist to make corrective interventions, if necessary, in a simpler manner.

It is possible for the user to display the plasma concentration and the effect compartment concentrations, which are reached on the basis of the drug boli or infusion rates set manually, with future prediction. In addition, automatic dispensing is possible to reach certain effect compartment concentrations specified by the user for at least two drugs.

It is also possible to evaluate the instantaneous drug concentrations concerning their distance from isoboles of specific, anesthesia-relevant end points, e.g., the awakening isobole or the isobole that predicts the tolerance of laryngoscopy. The awakening isobole can be determined from interaction models and the maximum concentrations for spontaneous breathing. The user can also display for himself the context-sensitive awakening time as the distance in time from the awakening isobole.

The anesthesia device offers the possibility of actuating the means for feeding anesthetics in a quantitatively settable, controlled manner, e.g., injection pumps, such as to reach a preset concentration in the plasma or at the site of action after a short time. In case of the dispensing of two or more anesthetics simultaneously, the changes in the concentrations take place along or at a flat angle to the action isoboles. The change in the concentrations at a flat angle to the isoboles is necessary when it is necessary to switch over between two concentration combinations and greatly different saturation or elimination times will compete in such a way that a trajectory with which the anesthesia will become massively deeper could develop.

The anesthesia device can be operated in an active mode and a passive mode. In the passive mode, anesthesia action parameters are evaluated and displayed in the manner being described here. In addition, the predictions of the module for pharmacokinetic compartment model calculations are used in the active mode to control the current rates of dispensing by comparison with target concentrations and to automatically set the means for the dispensed feed of the anesthetics.

A compensation of the fentanyl kinetics with remifentanyl is implemented in the anesthesia device to maintain a preset concentration. Increasing amounts of remifentanyl are administered during the phase of elimination of fentanyl in order to maintain the target concentration at the site of action at a constant value. Conversely, the remifentanyl dosage is reduced or even stopped altogether for a certain period of time in case of a bolus dose of fentanyl, so that the fentanyl concentration will again drop below the target concentration and remifentanyl must be supplemented.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
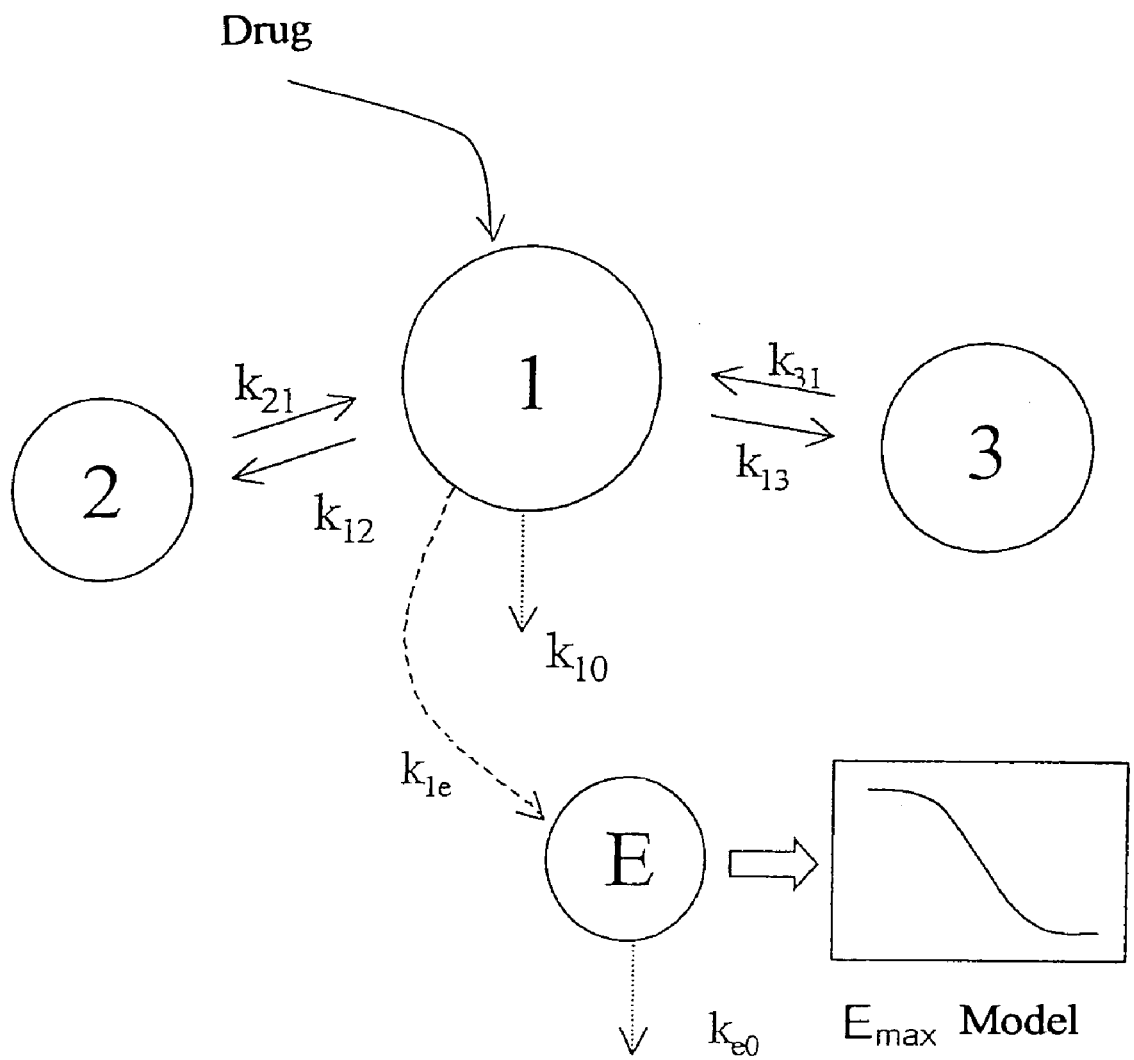
FIG. 1 is a schematic view of a pharmacokinetic compartment model.

Referring to the drawings in particular, FIG. 1 shows a schematic view of a mamillary three-compartment model with a central compartment 1, two peripheral compartments 2, 3 and an effect compartment E. The drug is administered exclusively into the central compartment 1, and the elimination takes place exclusively from the central compartment 1. There is no explicit mass transport into the effect compartment E, arrow drawn in broken line, kle. The concentration ratio between the central compartment 1 and the effect compartment E is indicated by ke0. The concentration in the effect compartment E is correlated with the action independently in time.

Figure 3:
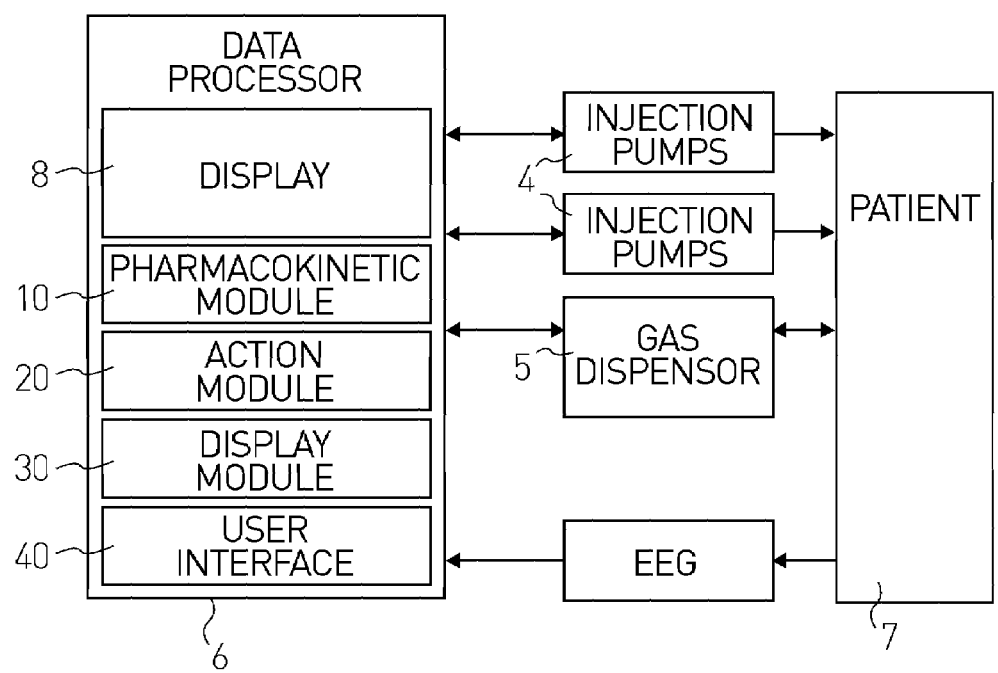
FIG. 3 is a schematic block diagram showing the functional units of the anesthesia device.

A data processing means 6 is provided in the anesthesia device according to the present invention. As is shown in FIG. 3, the data processing means 6 comprises a module 10 for pharmacokinetic compartment model calculations, which is set up to perform corresponding compartment model calculations for the different anesthetics of interest on the basis of the continuously entering rates of administration of the individual anesthetics. As a result, a continuously updated sequence of concentration values is provided for the anesthetics of interest, which reflect the course of anesthesia through the sequences of concentration values of the individual anesthetics.

Provisions are made for the module 10 for pharmacokinetic compartment model calculations to be also used to calculate concentration values for each anesthetic for one point in time or for a plurality of points in time, making the assumption that the administration of the anesthetics is continued constantly.

The module 10 for the compartment model calculations may be embodied either in a separate arithmetic unit or implemented as a program section of the data processing means 6.

Figure 2:
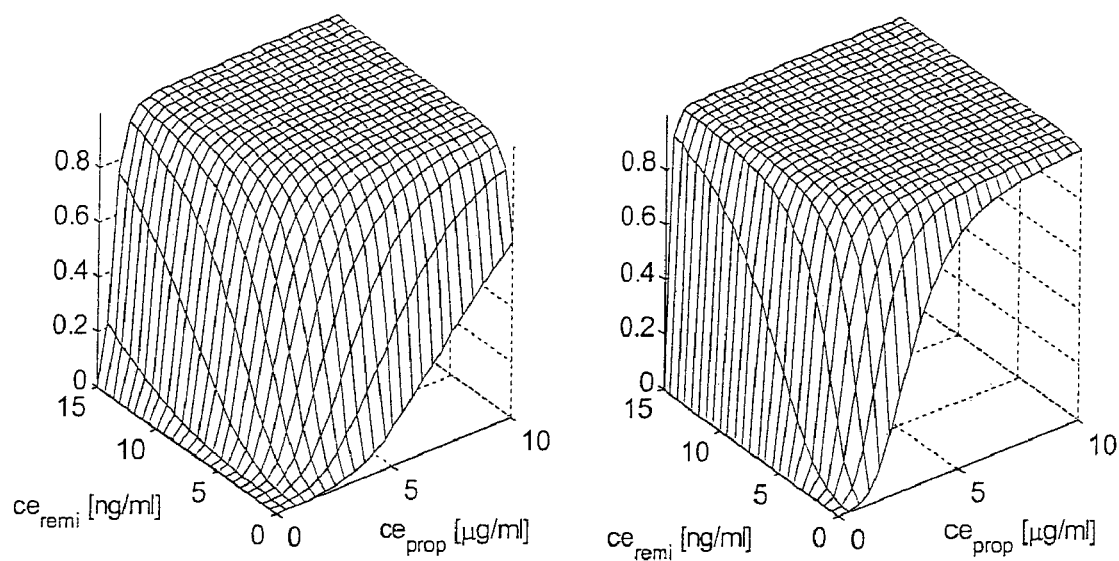
FIG. 2 is a view with diagrams showing the action surfaces (response surfaces) for the probability of the tolerance of laryngoscopy (TOL), left-hand figure, and that of the tolerance to shaking and shouting (TOSS), right-hand figure, as a function of the concentrations of the anesthetics propofol and remifentanyl.

Furthermore, a so-called action module 20, which keeps ready the curve of at least one anesthesia action parameter as a function of the concentrations of the first and second anesthetics, is provided in the data processing means. Such an anesthesia action parameter may be, e.g., the probability of tolerance of laryngoscopy (TOL) and that of the tolerance to shaking and shouting (TOSS). Another anesthesia action parameter may be "MAC Awake" which is known as the minimum alveolar concentration (MAC) of inhaled anesthetics that suppresses the appropriate response to command in 50% of subjects. This dependence of the anesthesia action parameters on the concentrations of two anesthetics used can be represented in a three-dimensional system of coordinates, in which the x and y axes show the concentration of the first and second anesthetic, respectively, the respective anesthesia action parameter being shown on the x axis. Examples of two such so-called response surfaces are shown in FIG. 2, namely, the response surfaces for the probability of the tolerance of laryngoscopy (TOL) and the tolerance to shaking and shouting (TOSS) for the anesthetics propofol and remifentanyl. Such response surfaces are obtained by statistical analyses on volunteers and on patients. The response surface can also be adapted over time in a patient specific manner. The response surfaces can be parametrized and stored in the parametrized form; as an alternative, it is possible to store a plurality of isoboles, i.e., lines of equal action, which are formed on cutting the response surfaces with a plane that is parallel to the x-y plane, and which can likewise characterize the course of the response surface if they are available in a sufficient number.

Furthermore, the data processing means 6 is provided with a display module 30. The display module 30 receives the concentration data from the module 10 for pharmacokinetic compartment model calculation as well as data from the action module 20, which characterize the response surface. The display module 30 is set up to actuate a display means 8, so that at least one action diagram will be displayed on it. The concentrations of the first and second anesthetics are plotted on the x and y axes in this action diagram. The sequence of concentration values up to the current point in time is represented in this x-y system of coordinates as a sequence of dots, which represents the course of the anesthesia. Furthermore, the display module 30 superimposes to the x-y system of coordinates a view of the response surface of a selected anesthetic action parameter. This superimposition can be performed, e.g., by projecting the response surface into the x-y planes by assigning to each point of the x-y plane an intensity that corresponds to the value of the response surface at that point or to the corresponding tristimulus value of a color scale set previously.

In a preferred embodiment, the display module 30 performs the projection of the response surface into the x-y diagram of the concentrations of the first and second anesthetics by a plurality of isoboles of the response surface being projected into the x-y plane and by the surfaces located between adjacent isoboles being covered with different colors. It is, in turn, advantageous to assign a color scale to the isobole values in advance, so that, e.g., critical areas of the anesthetic action parameter are marked by a correspondingly intense red color, middle areas by an increasingly yellow color, and noncritical areas by an increasingly intense green color. The representation of a plurality of isoboles in the x-y plane of the concentrations corresponds to the representation of contour lines for the response surface, which is shown three-dimensionally in FIG. 2.

Figure 4:
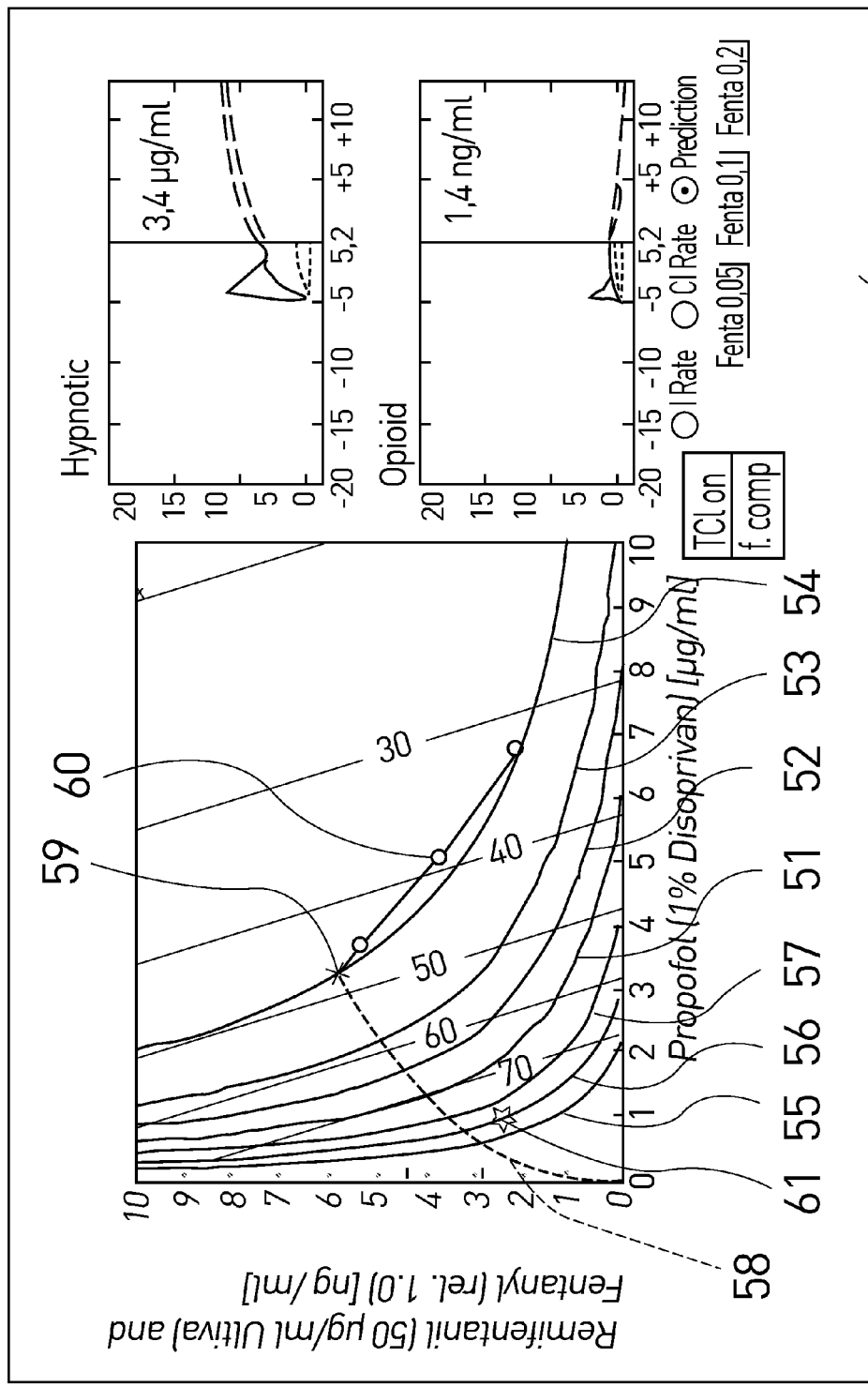
FIG. 4 is a view of the anesthesia device showing different displays.

An exemplary view of the display means 8 is shown schematically in FIG. 4. The concentration of remifentanyl is shown on the y axis and the concentration of propofol on the x axis. Furthermore, four isoboles 51-54, namely, for 25%, 50%, 75% and 95% probability that no reaction will develop, are shown for the anesthetic action parameter in case of probability of tolerance of laryngoscopy (TOL). Furthermore, three isoboles 55, 56, 57 are shown, which show the 25%, 50% and 75% probability that the patient does not respond to loud shouting and shaking (anesthesia action parameter TOSS).

Furthermore, the display module displays the sequence of concentration data of the first and second anesthetics as a sequence of points 58, which are connected to one another as a trajectory. The current status is indicated by a cross 59. The line originating from the end of the trajectory with three circle symbols 60 shows the predicted concentration data for the status in 1, 5 and 15 minutes in case the further rate of infusion is unchanged.

Furthermore, the module 10 for the pharmacokinetic compartment model calculations performs a model calculation for the assumption that the feed of the anesthetics is immediately interrupted. The point in time at which the awakening curve is intersected with, e.g., 50% TOSS, which corresponds to the hypothetical point of awakening in case of immediate interruption of the feed of anesthetic, is then determined in the module 10 for pharmacokinetic compartment model calculation. This expected awakening time is displayed in the display unit. The concentration data of the anesthetics, which are then predicted, are displayed by a separate asterisk symbol 61. The data processing means 6 can also have an awakening time prognosis module, which is set up for calculating a predicted awakening time on the basis of the current concentrations of the first and second anesthetics. An awakening isobole can be determined from interaction models and the maximum concentrations for spontaneous breathing. The awakening time prognosis module sends the predicted awakening time on the basis of the current concentrations to the display module, which displays the predicted point in time of awakening in the action diagram at the concentrations of the first and second anesthetics, which concentrations are predicted for that point in time of awakening. p Two windows, in which the concentrations of the individual anesthetics are shown, are shown next to the action diagram in the display means shown in FIG. 4. The concentration curve from the beginning of the anesthesia procedure to the current point in time (vertical line) as well an extrapolation with predicted concentration values for about 15 minutes into the future are displayed here.

The schematic block diagram of the anesthesia device according to FIG. 3 comprises a data processing means 6 and a display means 8. The data processing means 6 has a user interface 40, via which the anesthesiologist can enter settings to set the anesthetics fed intravenously or by inhalation. The data processing means 6 acts for this purpose on injection pumps 4 in a controlling manner and for the administration of intravenous anesthetics and a gas dispensing means 5 for adding gaseous anesthetics, such as desflurane, sevoflurane, isoflurane and enflurane, in order to set these corresponding to the requirements for the patient 7.

The arrows in FIG. 3 shall schematically indicate interfaces and transported data. During operation, the injection pumps 4 continuously supply data on the current rates of infusion and other data, which are useful for the determination of the status in the data processing means 6. If gaseous anesthetics are administered, the data processing means 6 acts on the gas dispensing means 5 in a controlling manner.

The action module 20 and the display module 30 may be embodied each in a separate arithmetic unit or implemented as program parts in the data processing means.

While specific embodiments of the invention have been shown and described in detail to illustrate the application of the principles of the invention, it will be understood that the invention may be embodied otherwise without departing from such principles.

What is claimed is:

1. An anesthesia process, comprising the steps of:
    providing a feed device for feeding at least a first anesthetic and a second anesthetic in settable quantities;
    providing a display;
    providing a data processing unit connected to the display;
    providing a pharmacokinetic compartment model calculation module to determine current concentrations of a first anesthetic and a second anesthetic in a plasma or at a site of action and to store concentrations of said first anesthetic and said second anesthetic continuously as a time sequence of concentration data, wherein concentration data of the first and second anesthetics predicted for at least one point in time in the future are also calculated by means of the pharmacokinetic compartment model calculation module;
    providing response curves for at least one anesthesia action parameter as a function of the concentrations of the first and second anesthetics; and
    displaying on the display at least one action diagram, in which the concentrations of the first and second anesthetics are displayed on a first axis and a second axis respectively, wherein response curves are superimposed to a system of coordinates of the first and second axis, said displaying includes displaying the sequence of the concentration data of the first and second anesthetics as a sequence of points, which are connected to one another as a trajectory, displaying a current concentration status with a symbol and displaying predicted concentration data with a separate symbol.

2. An anesthesia process in accordance with claim 1, wherein the concentration data of the first and second anesthetics predicted for at least one point in time in the future are also calculated under an assumption of a feed continued in a defined manner.

* * * * *

UNITED STATES PATENT AND TRADEMARK OFFICE
CERTIFICATE OF CORRECTION

| | | |
|---|---|---|
| PATENT NO. | : 7,556,036 B2 | Page 1 of 1 |
| APPLICATION NO. | : 11/250026 | |
| DATED | : July 7, 2009 | |
| INVENTOR(S) | : Bouillon et al. | |

It is certified that error appears in the above-identified patent and that said Letters Patent is hereby corrected as shown below:

The first paragraph of the letters patent incorrectly states that priority is claimed to German Application DE 10 2004 050 717.1, filed on October 19, 2005.

The correct date is October 19, 2004.

Signed and Sealed this
Eighteenth Day of December, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,556,036 B2 | Page 1 of 1 |
| APPLICATION NO. | : 11/250026 | |
| DATED | : July 7, 2009 | |
| INVENTOR(S) | : Bouillon et al. | |

It is certified that error appears in the above-identified patent and that said Letters Patent is hereby corrected as shown below:

Column 1, line 9,

The first paragraph of the letters patent incorrectly states that priority is claimed to German Application DE 10 2004 050 717.1, filed on October 19, 2005.

The correct date is October 19, 2004.

This certificate supersedes the Certificate of Correction issued December 18, 2012.

Signed and Sealed this
Twenty-sixth Day of February, 2013

Teresa Stanek Rea
*Acting Director of the United States Patent and Trademark Office*